United States Patent [19]

Newton et al.

[11] Patent Number: 5,415,878
[45] Date of Patent: May 16, 1995

[54] SLOW RELEASE COMPOSITIONS

[75] Inventors: John M. Newton; Jing Qui, both of London; Paul O'Brien, Bedford, all of England

[73] Assignee: London School of Pharmacy Innovations Limited, London, England

[21] Appl. No.: 39,391

[22] PCT Filed: Aug. 29, 1991

[86] PCT No.: PCT/GB91/01452

§ 371 Date: Apr. 21, 1993

§ 102(e) Date: Apr. 21, 1993

[87] PCT Pub. No.: WO92/04032

PCT Pub. Date: Mar. 19, 1992

[30] Foreign Application Priority Data

Aug. 29, 1990 [GB] United Kingdom ............... 9018839

[51] Int. Cl.⁶ .................. A61K 33/00; A61K 33/24; A61K 33/06; A61K 9/32
[52] U.S. Cl. ................... 424/722; 424/617; 424/482; 424/682
[58] Field of Search .......... 424/715, 722, 617, 482; 423/598, 610; 514/964, 965, 600

[56] References Cited

U.S. PATENT DOCUMENTS

| 2,111,460 | 3/1938 | Rockstroh | 423/598 |
| 3,639,100 | 2/1972 | Rick | 23/202 V |
| 3,641,236 | 2/1972 | Coppen et al. | 424/715 |
| 3,779,926 | 12/1973 | Merck et al. | 252/62.1 |
| 4,207,297 | 6/1980 | Brown et al. | 423/179.5 |
| 4,264,573 | 4/1981 | Powell et al. | 424/19 |
| 4,567,031 | 1/1986 | Riley | 423/593 |
| 4,689,211 | 8/1987 | Nishuichi et al. | 423/598 |
| 4,789,613 | 12/1988 | Ohtani et al. | 430/110 |
| 4,806,331 | 2/1989 | Adams, Jr. et al. | 423/430 |
| 4,919,723 | 4/1990 | Wilhelm et al. | 106/441 |
| 4,938,967 | 7/1990 | Newton et al. | 424/458 |
| 4,985,078 | 1/1991 | Rademachers et al. | 106/419 |

FOREIGN PATENT DOCUMENTS 0093538 11/1983 European Pat. Off. .
0619568 10/1935 Germany .

*Primary Examiner*—Allen J. Robinson
*Assistant Examiner*—Deborah Lambkin
*Attorney, Agent, or Firm*—Ostrolenk, Faber, Gerb & Soffen

[57] ABSTRACT

Lithium titanate is made by heating to a temperature of at least 715 C., powder form lithium carbonate and titanium dioxide while mixing, for instance in a rotary kiln. The product is formulated into extended release oral pharmaceutical compositions. Lithium ions are released by zero order rate characteristics from the compositions. The composition can have increased density to extend retention in the stomach. The compositions are used for treatment of manic depressive illness.

19 Claims, 2 Drawing Sheets

SLOW RELEASE COMPOSITIONS

The present invention relates to slow (or extended) release compositions which release metal ions into their surrounding environment over an extended period of time. A preferred embodiment of the invention relates to slow release orally administered pharmaceutical or veterinary compositions for releasing monovalent metal ions to a human or animal, especially compositions containing lithium ions.

Controlled release drug delivery systems are designed to achieve a prolonged therapeutic effect by releasing active ingredient into their surroundings over an extended period of time. The use of sustained release compositions allows optimisation of delivery of the active ingredient to the site of absorption and to achieve availability of the active ingredient at its site of action. Controlled release systems are of particular value where the active ingredient is to be supplied over an extended period, for instance during long term, continuous treatment, such as for treatment of nervous disorders such as mania and depression.

Most controlled release systems release active ingredient at a rate which is not zero-order, that is the rate of release changes over time. Usually the rate of release gradually decreases as the time from administration increases. This tends to provide a level of circulating active ingredient in the body which is not constant, which is undesirable. Attempts have been made to provide sustained release compositions with zero order release characteristics. Osmotic pump devices are intended to give zero order rate characteristics but in practice the rate of release of active ingredient reduces as time goes on. Tablets have been provided with complicated shapes, for instance of hollow cylindrical shape, in order that their surface area remains substantially constant throughout their dissolution, but in practice such compositions do not give the desired zero-order release characteristics.

Lithium ions have long been used in the prophylaxis and treatment of manic depressive illness. Lithium has also been used to augment the anti-depressant effect of other anti-depressants and to treat particularly types of headaches. It is generally used in oral dosage forms, for instance comprising lithium carbonate in capsule or tablet form, or more rarely in syrup form. A lithium carbonate extended release tablet is available commercially. It is important that the concentration of lithium in the serum is maintained below toxic levels, which can be very close to therapeutic levels. Equally, particularly during manic episodes, the serum concentration should be maintained at levels sufficiently high for it to be of therapeutic value. An improved form of lithium-containing composition which satisfies these requirements is desirable.

Figure 1:
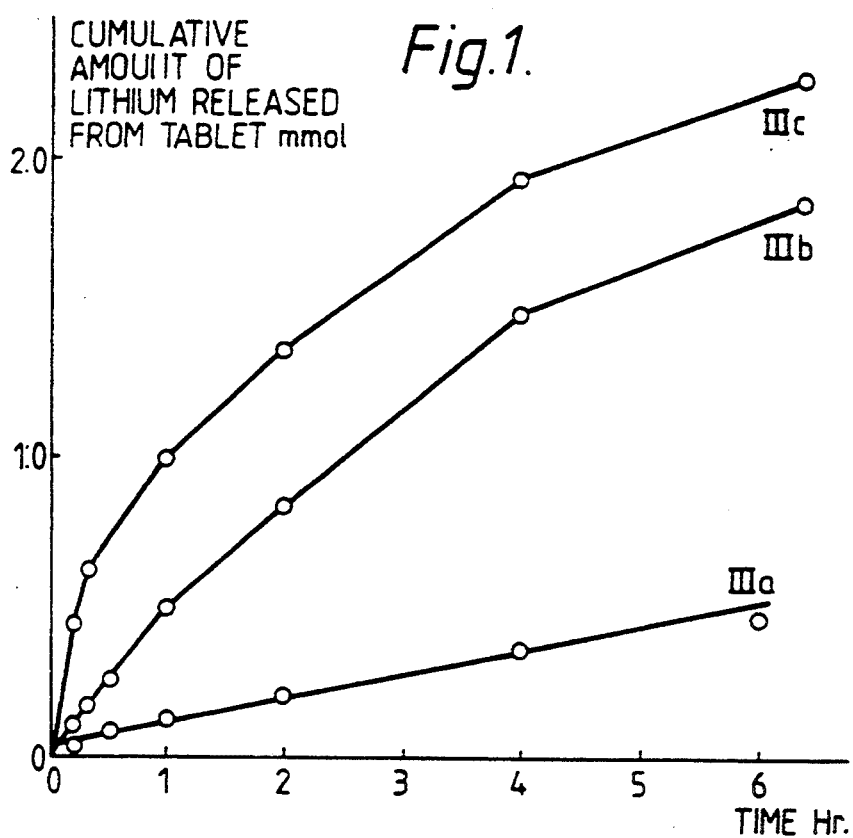
FIG. 1 shows the cumulative amount of lithium released from tablets.

According to the present invention there is provided an extended release composition comprising a compound of the formula I $$M_nXO_3 \quad\quad\quad I$$

in which M is a mono- or di-valent metal ion, n is 2 when M is mono-valent and 1 when M is di-valent and X is a group IVa element.

M is generally a mono-valent metal ion, as such ions are releasable at a satisfactory rate from the composition. Under some circumstances, for instance where a slow rate of release is desired and where the composition releases the ion over a very long period, di-valent metal ions may be suitable, for instance of zinc, magnesium, copper (11) or manganese. Mono-valent metal ions are for instance copper (1), or more usually alkali metal ions, for instance lithium, sodium or potassium. The invention is of particular value for compounds where M is lithium.

Although X may be any group IVa element, it is most usually the most common of these, namely titanium. The invention may, however, also be of value for compounds where X is hafnium or zirconium.

The compositions allow sustained release of $M^{(2/n)+}$ ions into surrounding, aqueous environments. The inventors have found that the compositions release the metal ion by zero order rate characteristics which is often desirable for the reasons mentioned above. The compositions may for instance be for use in agriculture, to release trace elements to crops or live stock. Alternatively the compositions may be in combination with slow release organic compounds, e.g. pesticides or other biologically active compounds where the presence of $M^{(2/n)+}$ augments that activity. The compositions may be for veterinary use, again for continuous, slow release of metal ions from orally administered compositions. The compositions may be for addition of trace elements or delivery of metals that are toxic to biological contamination to water systems or for addition to aqueous liquors for treatment of fish or other aquatic organisms.

The invention is of most value in the provision of pharmaceutical compositions, for oral administration to human beings. The invention is of particular value where M is lithium, so that the composition is for sustained release of lithium ions to a patient, for instance suffering from manic depressive illness.

The inventors have found that when the compound is lithium titanate then, in common with other inorganic lithium salts, the compound is relatively insoluble in aqueous media at neutral and alkaline pH's but relatively soluble in acid. This makes compositions containing lithium compounds of the formula I particularly useful for oral pharmaceuticals where release of active ingredient into the stomach is required. The combination of the zero-order release characteristics and acid-solubility are particularly advantageous.

According to a further aspect of the invention there is provided a compound of the formula I $$M_nXO_3 \quad\quad\quad I$$

wherein M, n and X are as described above, for a new use in the treatment of a human or an animal by therapy.

Oral compositions for use as pharmaceuticals, in particular for human treatment, are for oral administration and are provided in otherwise conventional form. Thus the compositions may be in the form of tablets, multiple unit doses, for instance comprising a plurality of pellets filled into granules or combined into a disintegratable tablet, or may be provided as powders in a sachet, or in the form of liquid suspensions. Where the composition is a tablet or a multiple unit formulation it will usually contain a pharmaceutically acceptable binder, which may act to bind the components and optionally also to provide additional controlled release characteristics. For instance tablets and pellets may be coated by conventional coating compositions. Preferably such binders act to retain the tablet or pellet intact within the stomach of a patient to whom the composition is administered, for at least the period within which the active ingredient is released. Usually the coating is permeable to water and to the active ingredient in any aqueous environment, especially in the stomach.

Compositions which are for veterinary use in ruminants may be provided in a form for extended residence in the rumenoreticulum for instance by being in the form of large and/or heavy boluses or by being provided with other means for retention known per se.

Compositions for application to non-animal environments may be in powder, dispersion, granules, pellet, tablet, block, or any other suitable form.

The compositions are generally made from the compound in powder form, by conventional formulation techniques, including tableting, granulation, pelletisation and other methods known per se.

There is also provided in the invention a method of producing the new compositions by a process in which powder form $XO_2$ is heated with a powder form compound of the formula $M_{n'}A_m$, in which A is an anion and m and n' are integers appropriate for the valencies of the metal ion and the anion and then formulating the product into the composition. The heating process is such as to decompose with release of a gas, so that the compound of the formula I is the sole solid product. The heating may be carried out in an oxidising atmosphere such as in air or other oxygen-containing gas. A is an anion which, when $M_nA_m$ is heated forms a gas and $M_{2/n}O$. The anion is chosen such that the heating temperature is as low as possible. The reaction preferably does not form any solid by-products. Suitable anions are formate, oxalate, nitrate, nitrite, hydroxide and, most preferably carbonate. Sulphate and phosphate may be used but require very high temperatures. Acetate may be used but can produce solid carbon in the absence of inadequate oxidation.

The two components are preferably used in approximately stoichiometric amounts although an excess of up to 50% of either component may be used. Preferably the excess of one or other of the components is less than 25%, preferably less than 20% and most preferably less than 10 or 5%. Any excess is generally of the component $M_{n'}A_m$ although an excess of $XO_2$ can give a desirable high density to the product and/or affect the rate of release.

The two components in powder form are heated together preferably whilst mixing, although mixing can be carried out prior to heating and then the static mixture can be heated. Heating is carried out to a temperature at which the reaction takes place, for a period which is adequate to allow the decomposition reaction of $M_{n'}A_m$ to go substantially to completion. The period for the reaction is in the order of several hours, usually at least 12 hours, preferably at least 15 hours, often more than 24 hours, although at higher temperatures the time can be shorter for instance less than 24 hours.

A reaction of the this type between lithium carbonate and titanium dioxide has been described by Onodera et al in "Chemistry and Industry", 19th Dec., 1988, page 786. The process is carried out by heating a 1:1 molar mixture of titanium dioxide (anatase) and lithium carbonate in air at 850° C. for 24 hours.

The present inventors have found that, at least where the starting materials comprise lithium carbonate, the temperature of the reaction should be at least 700° C., preferably at least 750° C. although temperatures above 800° C. are unnecessary. If the temperature is below about 700° C. then the release characteristics of the resultant product are not zero-order but instead tend to first order characteristics. Heating to a temperature of at least 715° C. is preferred.

Pre-mixing can be done in conventional apparatus such as a "tubular mixer" or by grinding the powders together either dry or in a liquid non-solvent for the powders, followed by drying of the resultant slurry. Static heating can be done in a furnace e.g. a muffle furnace. The reaction is preferably carried out whilst the two components are being mixed for instance in a rotary kiln.

Alternatively the powders can be compressed to form tablets and then heated whilst being compressed in the mould. In such a process care must be taken to allow release of any gas bi-product from the mould. By this process the product may not require further compounding before use.

The starting materials are provided in the form of powders. In general it is found desirable for the particle size of the starting materials to be less than 200 μm, preferably less than 100 μm, for instance it is preferred for the median particle size to be in the range 50 to 5 μm, preferably 30 to 15 μm.

The compound of the formula I is often a very dense solid, which has a density of well over 3.0. Titanium dioxide, the starting material for making the preferred compounds, has a density of 3.6 and the densities of titanates formed from it also tend to be more than 3. For instance the density of lithium titanate is around 3.46 g/ml. For some of the slow release compositions of the invention it is desirable for the composition itself, ie including binders, excipients and other ingredients, ailments to have a high density, for instance a density of at least 2.5 g/ml or higher, preferably at least 3.0 g/ml. In particular controlled release pharmaceutical compositions for oral administration to humans have been shown to have extended gastric residence times in fed and fasted patients, which further enhances the slow release characteristics of the compositions. This phenomenon is described in EP-A-0265061.

According to a particularly preferred aspect of the invention there is provided a new extended release oral pharmaceutical composition which comprises controlled release units containing a compound of the formula I $$M_nXO_3 \qquad \qquad I$$

wherein M, n and X are as described above, preferably in which X is titanium, preferably in which M is alkali metal (most preferably lithium), the individual units having a density of at least 2.5 g/ml.

According to a further aspect of the invention there is provided a new use of a compound of the formula I $$M_nXO_3 \qquad \qquad I$$

wherein M, n and X are as described above, preferably in which X is titanium, preferably in which M is an alkali metal, most preferably lithium in the manufacture of a composition for use in the treatment of a human or animal by therapy. The composition is usually an extended release composition.

Since the composition containing a compound of the formula I in which M is an alkali metal releases the alkali metal ion with zero-order rate characteristics, it is generally unnecessary for the release to be further controlled by the provision of a controlled release binder for the composition. A controlled release binder is, in this context, a coating or a matrix binder which affects the rate of release of active compound from the composition. That type of control may be effected by providing a coating which is permeable to the aqueous environment of some areas of the gastro-intestinal (GI) tract only, for instance by being permeable in alkaline but not acidic environments, so that active ingredient is released beyond the stomach but not in the stomach. In some circumstances the provision of such binders may be advantageous. Where the compositions have high densities, for instance more than 2.5 g/ml, it is desirable for the active ingredient to be released in the stomach since the residence time of the compositions is higher than normal, so that any controlled release binder should allow release of the active ingredient into the stomach at least.

The following examples illustrate the invention:

EXAMPLE I: THE PREPARATION OF LITHIUM TITANIATE

The product lithium titaniate was prepared by heating the mixture of lithium carbonate powder and titanium dioxide powder at higher temperature in the furnace. The details were described as below.

1] MATERIALS

Lithium carbonate powder and titanium dioxide were used in the preparation of lithium titaniate.

The initial particle size of both powder was measured by Malvern laser sizer. The results were shown in Table 1.

TABLE I

| Initial Particle Size of $Li_2CO_3$ and $TiO_2$ | |
|---|---|
| Raw Materials | 50% under ($\mu$m) (medium diameter) |
| $Li_2CO_3$ | 27.56 |
| $TiO_2$ | 10.10 |

2] CHEMICAL REACTION

A certain amount of lithium carbonate powder and titanium dioxide powder in 1:1 molar ratio was accurately weighed. About 25 g of the mixture of powders was mixed with TURBULAR mixer for about 20 minutes until a uniform mixture was obtained. Then, the mixture was transferred to a container which is stable at high temperature inside a muffle furnace. It was heated at a temperature between 715° C. and 755° C. for various periods in air. The results showed that for reaction to take place and to give a compound having zero order release characteristics, the heating temperature had to be over 715° C. and the heating time is at least 15hr.

EXAMPLE II : THE PREPARATION OF FINAL TABLETS

1] MATERIALS

The following materials were used: lithium titanate produced by the process described in example I by heating at at least 715° C. for at least 15 hours, polyvinylpyrrolidone (PVP), and magnesium stearate.

2] PREPARATION OF TABLETS

The powder of lithium titanate was mixed with a certain amount of 5% PVP aqueous solution, as a binder, to produce a wet mass. The wet mass was screened by sieve No. 1 to produce wet granules. The wet granules were dried at 85° C. for 25 minutes and mixed with 1% mangesium stearate incorporated as a lubricant prior to compression. Tablets were compressed on a single-punch F3 tablet machine MANESTY, at a tablet weight of 250 mg or 350 mg, using a flat faced punch of 8.5 mm diameter.

3] PROPERTIES OF TABLETS

The volume of tablets was measured by BECKMAN MODEL 930 AIR COMPARISON PYGNOMETER. The weight of tablets was obtained by weighing with a balance. The density of tablets was calculated and found to be well over 3.20 g/ml.

EXAMPLE III: RELEASE OF LITHIUM IN VITRO

1] METHOD

The release of lithium ions from final tablets was carried out by the USP paddle method, using a PHARMA dissolution tester. The dissolution medium was 1,000 ml of 0.1M HCl solution at 37° C. and the rotation velocity was 100 rpm. 2 ml of sample was withdrawn at following time intervals: 0.25 hr, 0.5 hr, 1 hr, 2 hr, 3 hr, 4 hr, 5 hr, 6 hr. Samples were filtered, diluted and analysed for Li by PERKIN-ELMER 280 atomic absorption spectrophotometer at 670.8 nm.

2] FACTORS EFFECTING THE RELEASE (a) Mixing System

The following mixing systems were used in the study: TURBULAR MIXER (TUR), MAGNETIC STIRRING SYSTEMS (MS) and McCHRONE MICRONISING MILL (MMM). The mixtures of lithium carbonate and titanium dioxide at 1:1 molar ratio were mixed by three mixing systems above for 10 minutes and heated at 760°-790° C. for 24 hr. The products of lithium titanate were formulated and tabletted with the method mentioned in Example II. The results of the release tests were shown in FIG. 1. The density of tablets and the mixing systems are shown in Table II.

TABLE II

| The Density of Tablets by Different Mixing Systems | | |
|---|---|---|
| Example | IIIa | IIIb | IIIc |
| Mixer | TUR | MS | MMM |
| Density (g/ml) | 3.19 | 3.32 | 3.30 |

The results of the release tests are shown in FIG. 1 indicate that the TUR mixing system gives the best zero order rate of release. For some applications the amount of lithium released from the tablets maybe however too low to be useful.

(b) Heating Temperatures

Six heating temperatures were used in the study (see table III.). The final tablets were made with the same method described in section II. The density of tablets is shown in table III.

TABLE III

| | Heating Temperature and the Density of Tablets | | | | | |
|---|---|---|---|---|---|---|
| Example | IIId | IIIe | IIIf | IIIg | IIIh | IIIi |
| Temp. (°C.) | 668–682 | 682–716.5 | 732–786 | 775–808 | 715–742 | 892–910 |
| Time (hr) | 24 | 24 | 24 | 24 | 24 | 3 |
| Density (g/ml) | 3.29 | 3.25 | 3.43 | | | |

Figure 2:
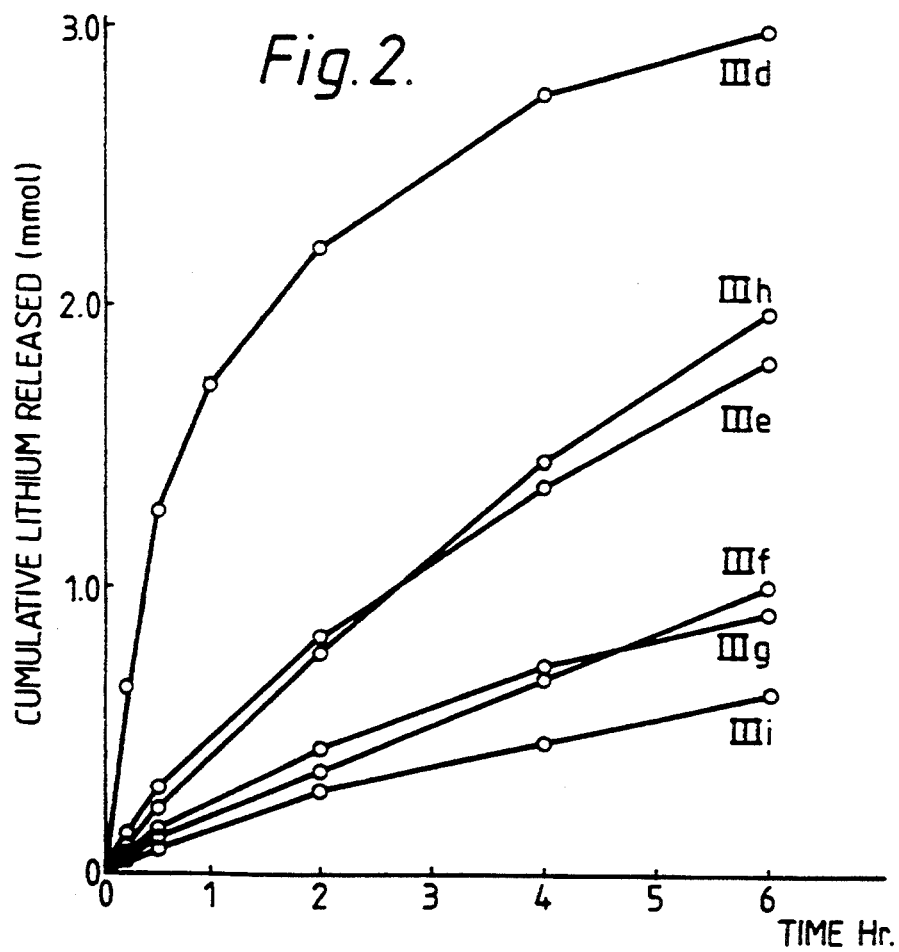
FIG. 2 shows the release of lithium at different heating temperatures.

The results of release of Li are shown in FIG. 2.

The conclusion can be drawn from the results above that lithium titanate is formed by heating at around 700° C. To obtain zero order release of lithium from the tablets, the heating temperature should be over 715° C. The rate of release of lithium from the tablets decreased with increase in the heating temperature.

(c) Different Heating Periods

Figure 3:
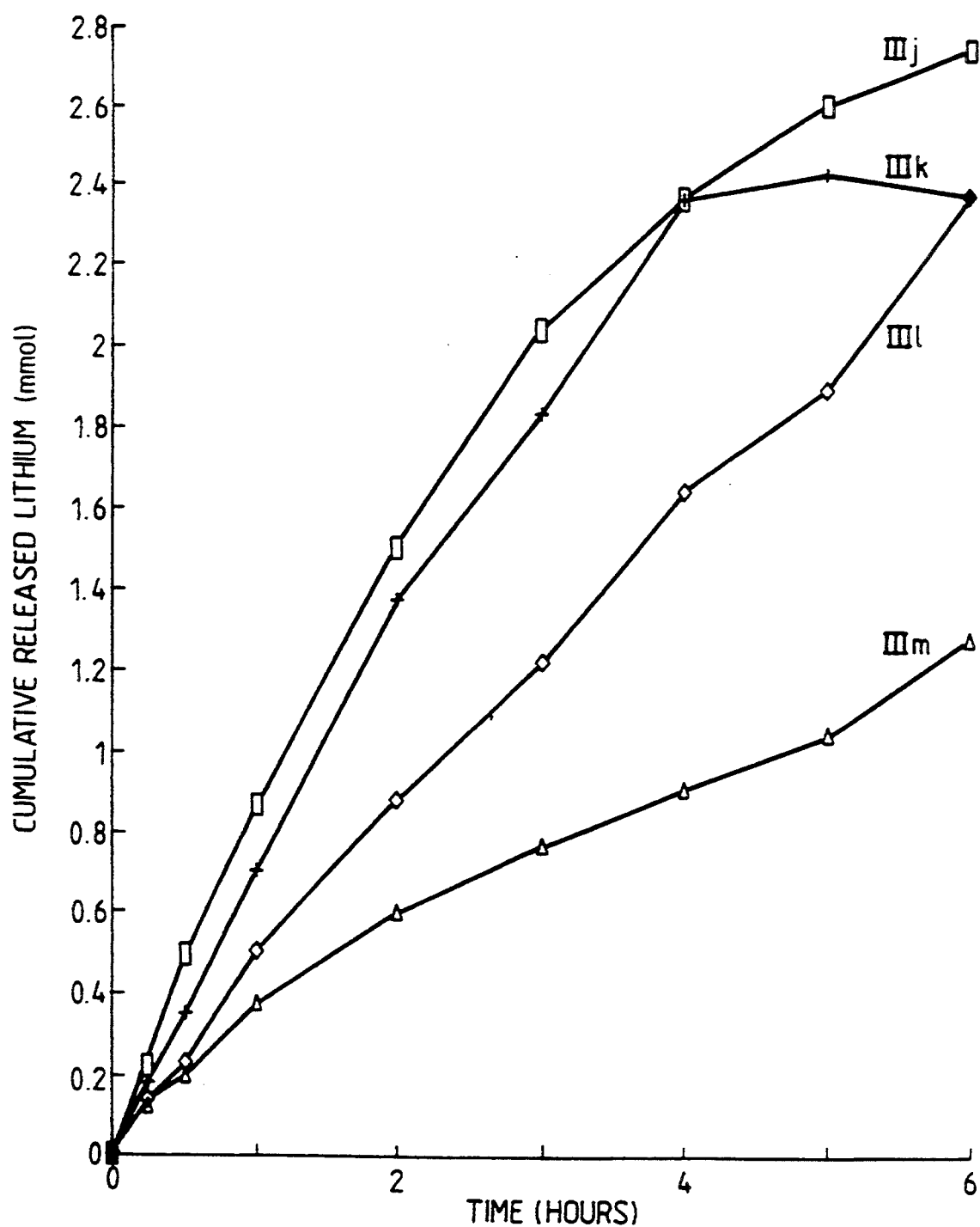
FIG. 3 shows the release of lithium at different heating periods.

The mixtures of lithium carbonate and titanium dioxide at 1:1 molar ratio were heated at 724° C.–744° C. for 3hr, 6hr, 15hr and 24hr (see table IV). The lithium titanate products were formulated and tabletted with the method described in Example II. The density of tablets is shown in table IV. The results of release of Li are shown in FIG. 3.

TABLE IV

| Heating Time and the Density of Tablets | | | | |
|---|---|---|---|---|
| Example | IIIj | IIIk | IIIl | IIIm |
| Time (hr) | 3 hr | 6 hr | 15 hr | 24 hr |
| Density g/ml | 3.29 | 3.34 | 3.37 | 3.35 |

From the results above, the conclusion can be drawn that the best heating time at 724° C.–744° C. is 15 hours. Under this heating condition, the release order of lithium is zero and the release amount of lithium from the tablets is not too low.

We claim:

1. A pharmaceutical composition comprising an extended release binder which is a pharmaceutically acceptable carrier and a compound of the formula $M_2TiO_3$ in which M is an alkali metal, in which said alkali metal is released from said composition when in contact with an aqueous environment.

2. A composition according to claim 1 in which M is potassium.

3. A composition according to claim 1 in which M is lithium.

4. The composition of claim 1, having a density of at least 2.5 g/ml.

5. The composition of claim 4, in which M is lithium.

6. A composition according to claim 1 in which said compound exhibits a zero order release rate characteristic when said composition is in contact with an aqueous environment.

7. The composition of claim 6, in which M is lithium.

8. In a method of treating human for manic depression by administering lithium, the improvement which comprises utilizing a composition comprising an extended release binder which is a pharmaceutically acceptable carrier and a compound of the formula $Li_2TiO_3$ in which said lithium is released from said composition when in contact with an aqueous environment.

9. A method of preparing a composition according to claim 1 in which a mixture of powdered titanium dioxide and powdered alkali metal compound are heated at a temperature of at least 700° C. and for a period of time of at least 12 hours which is sufficient to produce said compound and combining said compound with an extended release binder which is a pharmaceutically acceptable carrier such that the alkali metal is released when the combination is contacted with an aqueous environment.

10. The method of claim 9 in which the heating is continued for a time sufficient to produce said compound which exhibits a zero order release rate characteristic when in contact with the aqueous environment.

11. The method of claim 9 in which M is potassium.

12. The method of claim 9 in which M is lithium.

13. The process of claim 9 in which the stoichiometric excess of either of the two powders is no more than 20%.

14. The process of claim 9 in which the temperature is at least 715° C. and the time is at least 15 hours.

15. The process of claim 9 in which the powders are mixed during heating.

16. The process of claim 6 in which the powders are heated in a rotary kiln.

17. The process of claim 9 in which the powders have a particle size of less than 200 microns.

18. The process of claim 9 in which the powders have a particle size of less than 100 microns.

19. The process of claim 9 in which the mean particle size of the powders is in the range of 5 to 50 microns.

* * * * *